| United States Patent [19] | [11] Patent Number: 4,590,307 |
|---|---|
| Bennett, Jr. et al. | [45] Date of Patent: May 20, 1986 |

[54] CATALYST PRECURSOR PREPARED FROM MANGANESE CARBONATE, AND USE OF A CALCINED DERIVATIVE IN AN ORTHO-ALKYLATION PROCESS

[75] Inventors: James G. Bennett, Jr., Glenmont, N.Y.; Freddie L. Tungate, Georgetown, Ind.

[73] Assignee: General Electric Company, Pittsfield, Mass.

[21] Appl. No.: 719,762

[22] Filed: Apr. 4, 1985

Related U.S. Application Data

[62] Division of Ser. No. 563,311, Dec. 20, 1983, Pat. No. 4,547,480.

[51] Int. Cl.$^4$ ............................................. C07C 37/16
[52] U.S. Cl. ................................. 568/804; 502/174; 502/324
[58] Field of Search ..................... 568/804, 794, 789; 502/174, 324

[56] References Cited

U.S. PATENT DOCUMENTS

| 3,446,856 | 5/1969 | Hamilton, Jr. | 568/804 |
|---|---|---|---|
| 3,479,410 | 11/1969 | Hamilton, Jr. | 568/780 |
| 3,873,628 | 3/1975 | Van Sorge | 568/804 |
| 3,962,126 | 6/1976 | Pecak | 568/804 |
| 3,971,832 | 7/1976 | Watanabe et al. | 568/804 |
| 3,972,828 | 8/1976 | Van Sorge | 502/159 |
| 3,972,836 | 8/1976 | Van Sorge | 568/804 |
| 3,974,229 | 8/1976 | Van Sorge | 568/804 |
| 4,361,709 | 11/1982 | Kawamata et al. | 568/804 |
| 4,418,224 | 11/1983 | Bennett et al. | 568/804 |
| 4,503,272 | 3/1985 | Bennett, Jr. et al. | 568/804 |
| 4,528,407 | 7/1985 | Smith et al. | 568/804 |
| 4,547,480 | 10/1985 | Bennett et al. | 568/804 |

Primary Examiner—Werren B. Lone
Attorney, Agent, or Firm—Hedman, Gibson, Costigan & Hoare

[57] ABSTRACT

A catalyst precursor comprised of a dry admixture of manganese carbonate and at least one material selected from among magnesium carbonate, basic magnesium carbonate and magnesium hydroxide. The precursor is calcinable at elevated temperatures to an activated catalyst which may be used in a process for the ortho-alkylation of phenolic compounds.

10 Claims, No Drawings

CATALYST PRECURSOR PREPARED FROM MANGANESE CARBONATE, AND USE OF A CALCINED DERIVATIVE IN AN ORTHO-ALKYLATION PROCESS

CROSS-REFERENCE TO RELATED APPLICATION

This is a division of application Ser. No. 563,311, filed Dec. 20, 1983, now U.S. Pat. No. 4,547,480.

BACKGROUND OF THE INVENTION

Processes for the ortho-alkylation of phenolic compounds with an alcohol are known in the art. Typically, the reaction is carried out in the vapor phase using a metal-containing catalyst, for example, those based on magnesium alone or both magnesium and manganese. Various catalysts and methods for their preparation are described in the patent literature. For instance, magnesium oxide alone is useful as such a catalyst (Van Sorge, U.S. Pat. No. 3,972,828). Also suitable are finely divided mixtures of magnesium and manganese oxides (Van Sorge, U.S. Pat. Nos. 3,972,836 and 3,974,229). Mixtures of magnesium oxide and manganese sulfate are useful as well (Van Sorge, U.S. Pat. No. 3,873,628). These patents mention that the magnesium oxides may be derived by the thermal decomposition of magnesium carbonate.

Magnesium oxide as an ortho-alkylation catalyst is also disclosed in U.S. Pat. Nos. 3,446,856 and 3,479,410 (Hamilton).

More recent developments have involved the use of procedures in which catalyst precursors are first prepared by precipitating manganese hydroxide from a solution of a soluble manganese salt, onto magnesium carbonate or magnesium hydroxide, then activating the precursors by calcining it at elevated temperatures sufficient to form oxides. The resulting catalyst is uniform and provides good yields and good selectivity to the end product.

INTRODUCTION TO THE INVENTION

The discovery has now been made that powdered manganese carbonate can be dry blended with a magnesium containing material such as magnesium carbonate, basic magnesium carbonate or magnesium hydroxide, to form a catalyst precursor which, in turn, can be calcined to an active state by heating and used in a vapor phase process to prepare ortho-alkylated phenols.

This invention avoids the use of more complicated procedures for preparing catalyst precursors based on manganese and magnesium. By the language "dry blend" as used in this disclosure, it is meant that the individual ingredients are mixed together initially in the dry state, in a blender, a mechanical mixer, or the like, without resorting to "wet" techniques such as suspension blending or precipitation. Despite the absence of these more sophisticated procedures, adequate uniformity of the blended ingredients is obtained.

DESCRIPTION OF THE INVENTION

Manganese carbonate provides the only source of manganese in the catalyst. The magnesium moiety, on the other hand, can be provided by magnesium carbonate, basic magnesium carbonate or magnesium hydroxide, which can be used individually or in admixture with one another. The term "basic magnesium carbonate" refers to materials represented by the formula $$xMgCO_3 \cdot Mg(OH)_2 \cdot xH_2O$$

in which each x is independently a number average from about 3 to about 5.

In the preferred embodiments, basic magnesium carbonate, especially in finely divided particulate form, is used as the magnesium source.

It is also preferred that the manganese carbonate be present in a minor amount and the magnesium-containing material in a major amount, based on the weight of these ingredients combined. A sufficient amount of magnesium carbonate should be used to provide a manganese content in the blend of at least 0.1%, and preferably between 0.5 and 1.5% by weight of the magnesium-containing material.

By way of illustrating how the catalyst precursor may be prepared, in one procedure, powders of the ingredients, optionally containing a binder and/or shaping aid, are blended by rolling on a jar mill for 1½ to 2 hours. Any conventional binder material may be used, including a polymeric binder, for example, a polyphenylene ether (oxide) resin as described in U.S. Pat. Nos. 3,306,874 and 3,306,875 (Hay), preferably in amounts from about 0.1 to about 20% by weight. Poly(2,6-dimethyl-1,4-phenylene ether)resin is especially preferred. Similarly, any conventional shaping aid may be used, for example, powdered graphite in amounts of from about 0.1 to about 3.0% by weight.

The blend, comprised of the manganese and magnesium compounds together with any binder(s) and/or shaping aid(s) is then shaped into the desired physical form, for example, tablets, pellets, cylinders, and so forth. Illustratively, and preferably, the particulate blend is pressed into tablets, using standard tabletting equipment and procedures.

After being shaped, the catalyst precursor is treated to activate it for use in a reaction. This is done by heating the blend at a temperature of at least 300° C., and preferably from about 350° to about 500° C. A heating period of up to about 24 hours is normally sufficient to achieve activation at these temperatures.

The calcining treating may be carried out prior to loading the catalyst into the reactor, or alternatively, in situ in the reactor itself. Various environments can be used. For instance, calcination may be conducted in air, in an inert gas such as nitrogen, under vacuum, or in the presence of a feed mixture of the reactants for the process in which it is to be employed. Moreover, the manner in which the catalyst precursor is heated to calcine it is subject to variation. Thus, for instance, heat may be applied directly to the precursor particles as in an oven or by contact with the walls of the reactor chamber; or heating can occur through the phenomenon of convection, by contacting the particles with air, nitrogen or a feed mixture which has been preheated to the temperature required for catalyst activation.

During calcining, small pores form in the catalyst composite as the binder is decomposed, thereby exposing more surface area. At least 25, and especially from 25 to 450 square meters per gram is preferred, and this will normally occur using the conditions which have been described.

The catalyst is useful especially in reactions for the ortho-alkylation of phenolic compounds to effect or facilitate substitution on the ring. Such phenolic compounds are those having the formula

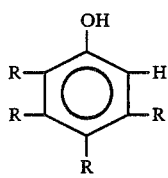

in which each R, independently, is a monovalent substituent selected from the group consisting of hydrogen, alkyl (preferably $C_1$ to $C_{12}$ alkyl), phenyl, and alkyl substituted phenyl (preferably $C_1$ to $C_{12}$ alkyl substituted phenyl).

The alkyl alcohol in the process is preferably a branched or linear saturated alcohol having up to about 16 carbon atoms, for example, methyl, ethyl, propyl, isopropyl, butyl, isobutyl, tert.-butyl, amyl, isoamyl, hexyl, heptyl, octyl, nonyl, decyl, lauryl, cetyl, cyclohexyl, and the like. Especially preferred are alcohols having up to 6 carbon atoms, methanol being the most preferred.

To illustrate such a process, a reaction feed mixture, comprising a phenolic compound or compounds and an alkyl alcohol, is vaporized and passed through a reactor which has been heated to a temperature of at least 300° C., and preferably from about 400° to about 500° C., and which contains the catalyst described above. For optimum results, it is advisable to employ at least one mole of the alkyl alcohol, and preferably from one to three moles, for each ortho position on the phenol to be alkylated. Thus, for example, if phenol, which has two ortho hydrogens per molecule, is to be methylated to produce 2,6-xylenol, it is best to use from two to six moles of methanol for each mole of phenol. The large yields will be obtained with use of the higher ratios of methanol to phenol.

The ortho-alkylation process can be carried out under various conditions of temperature, pressure, flow rate of reactants, vapor space velocity of reactants over catalyst, length of catalyst feed, and so on. Temperatures above 500° C. should be avoided, however, because decomposition of the reactants and/or products often becomes a problem.

In general, the reaction conditions are regulated to minimize the amount of feed materials which must be recovered and reused, and to maximize the percentage of selectivity to the desired ortho-alkylated end product, which is a phenolic compound having an alkyl substituent in the "2" or both the "2" and "6" positions on the ring.

The reaction will proceed at atmospheric pressure with good results, but superatmospheric or subatmospheric pressures are possible if desired.

The vapors emitted from the reactor are collected and condensed, and then separated into the individual constituents by conventional procedures, for instance, crystallization or distillation.

The process is useful for economically converting phenol to o-cresol, a disinfectant and preservative, and for converting both phenol and o-cresol to 2,6-xylenol, a monomer which can be polymerized to form poly(2,6-dimethyl-1,4-phenylene)ether(oxide), a high performance thermoplastic material.

DESCRIPTION OF THE SPECIFIC EMBODIMENTS

The invention is illustrated in the Examples below, which should not be construed as limiting.

EXAMPLE 1

A catalyst precursor in accordance with this invention was prepared by tumble mixing the ingredients listed below in a jar on a jar mill for ½ hour, then forming the resulting blend into 1/16 inch by 3/16 inch tablets.

| | |
|---|---|
| (basic) $MgCO_3$ | 225 grams |
| Poly(2,6-dimethyl-1,4-phenylene ether) (PPO ®, General Electric Co.) | 25 grams |
| $MnCO_3$ | 5.06 grams |

For comparison purposes, using the same procedure, two catalyst precursors in accordance with the prior art were prepared from the ingredients listed below.

| Comparison A | |
|---|---|
| (basic) $MgCO_3$ | 225 grams |
| PPO | 25 grams |
| MnO | 2.91 grams |
| Comparison B | |
| (basic) $MgCO_3$ | 225 grams |
| PPO | 25 grams |
| $Mn_3O_4$ | 3.26 grams |

EXAMPLE 2

The catalyst precursors prepared as described in Example 1 were evaluated in a process for the orthomethylation of phenol and o-cresol to form 2,6-xylenol, using the reactor described below. Calcination of the precursors took place in situ in the reactor in the presence of the alkylation feed mixture.

THE REACTOR

The Reactor is comprised of two stainless steel tubes, both disposed along a verticle axis, one of which has a length of 15 inches (38.1 centimeters), the other of which has a length of 24 inches (60.96 centimeters), and both of which have an inner diameter of ¾ inch (1.91 centimeters). The first functions as a vaporizer. The second is filled to a depth of two inches with glass beads serving as a support for the catalyst, and functions as a reactor. Both tubes are partially immersed in a fused salt bath, the first to a depth of 8 inches (20.3 cm), the second to a depth of 17 inches (43.2 cm). The first (vaporizer) and second (reactor) tubes are joined by a third tube, consisting of a two-inch long (5.1 cm) steel pipe connected at one end to an opening in the first tube 5 inches (12.7 cm) from its bottom, and at the other end to an opening in the second tube 14 inches (35.6 cm) from its bottom. The connector tube also passes through the fused salt bath.

In practice, a feed stream comprising the reactants is sent from a reservoir, through a metering pump, into the first (vaporizer) tube, where the feed stream is heated to a temperature high enough to volatilize the constituents. The vapors emitting from the vaporizer tube pass through the interconnecting pipe, which serves as a preheater to bring the vapors up to the temperature of the reactor tube. The vapors are fed from there to the reactor tube and the catalyst bed, where reaction takes place. Product vapors leave the bottom of the reactor tube through a stainless steel outlet tube, having an inner diameter of ⅜-inch (0.95 cm), and are led to a water-cooled condenser and receiver where they are liquified and recovered. The non-condensible materials are fed to an off-gas meter, where they can be measured.

In each instance, the reactor was charged with 110 milliliters of the catalyst precursor, then capped and placed in a 370° C. salt bath, immediately after which a stream of nitrogen gas was blown over the catalyst at a rate of 2 standard cubic feet per hour (SCFH). After a period of 15 minutes, the feed stream was introduced, which consisted of a 4:1 weight ratio of methanol to phenolics. The phenolics comprised a 60:40 weight ratio of phenol:ortho-cresol, containing about 20% water. A feed rate of 215 milliliters per hour was used, which was equivalent to a liquid hourly space velocity (LHSV) of 1.95. The reaction was conducted using standard pressure (1 atmosphere). The temperature was maintained at about 456° C. for the entire period. Periodically, the product stream was sampled and evaluated. The percentages of unreacted phenol and ortho-cresol, of 2,6-xylenol (the desired end product) and of 2,4,6-trimethyl phenol (a byproduct), as well as the selectivity to the desired end product were calculated, and the time weighted average results are reported in the Tables below.

TABLE 1

| MgCO₃/PPO/MnCO₃ (EXAMPLE 1) | | | | | |
|---|---|---|---|---|---|
| Time, hrs. | Off gas, SCFH | wt. % phenol | wt. % o-cresol | wt. % 2, 6 | wt. % 2, 4, 6 |
| 193 | 0.45 | 3.0 | 23.3 | 69.2 | 4.1 |
| 499 | 0.39 | 5.0 | 22.8 | 67.8 | 3.8 |
| TWA | 0.40 | 5.3 | 26.2 | 63.8 | 4.0 |

TABLE 2

| MgCO₃/PPO/MnO (Comparison A) | | | | | |
|---|---|---|---|---|---|
| Time, hrs. | Off gas, SCFH | wt. % phenol | wt. % o-cresol | wt. % 2, 6 | wt. % 2, 4, 6 |
| 193 | 0.31 | 5.2 | 31.9 | 59.0 | 3.4 |
| 499 | 0.31 | 6.0 | 25.5 | 64.8 | 3.3 |
| TWA | 0.27 | 8.0 | 32.7 | 54.9 | 3.4 |

TABLE 3

| MgCO₃/PPO/Mn₃O₄ (Comparison B) | | | | | |
|---|---|---|---|---|---|
| Time, hrs. | Off gas, SCFH | wt. % phenol | wt. % o-cresol | wt. % 2, 6 | wt. % 2, 4, 6 |
| 193 | 0.31 | 5.9 | 30.6 | 59.4 | 3.6 |
| 499 | 0.35 | 7.3 | 25.8 | 63.1 | 3.6 |
| TWA | 0.31 | 9.0 | 31.9 | 54.6 | 3/5 |

As can be seen, the best yield of 2,6-xylenol was obtained with use of a catalyst according to the invention (EXAMPLE 1, Table 1)—63.8% by weight, versus 54.9% (Comparison A, Table 2) and 54.6% (Comparison B, Table 3).

All of the above mentioned patents are incorporated herein by reference.

Other modifications and variations of the invention are possible in the light of the above disclosure. It is to be understood, therefore, that changes may be made in the particular embodiments shown which are within the scope of the invention defined in the appended claims.

We claim:

1. In a process for preparing an ortho-alkylated phenol by reacting in the vapor phase a branched or linear saturated alkyl alcohol having up to about 16 carbon atoms and one or more phenolic compounds represented by the formula

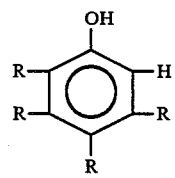

in which R is independently a monovalent substituent selected from the group consisting of hydrogen, $C_1$ to $C_{12}$ alkyl, phenyl and $C_1$ to $C_{12}$ alkyl substituted phenyl, in the presence of an alkylation catalyst, the reaction being conducted at a temperature of at least 300° C. at atmospheric, subatmospheric or superatmospheric pressure using at least one mole of the alkyl alcohol for each ortho position in the phenolic compound to be alkylated, the improvement wherein the alkylation catalyst is a calcined product derived by heating a dry mixture of manganese carbonate and one or more magnesium containing materials selected from the group consisting of magnesium carbonate, basic magnesium carbonate and magnesium hydroxide.

2. A process according to claim 1, in which the magnesium containing material is basic magnesium carbonate.

3. A process according to claim 1, in which the magnesium containing material is magnesium carbonate.

4. A process according to claim 1, in which the magnesium containing material is magnesium hydroxide.

5. A process according to claim 1, in which the catalyst has a manganese content of between 0.5 and 1.5% by weight of the magnesium-containing material.

6. A process according to claim 1, in which the catalyst has a surface area of at least 25 square meters per gram.

7. A process according to claim 1, in which the catalyst has a surface area of from 25 to 450 square meters per gram.

8. A process according to claim 1, in which the reaction is conducted at a temperature of from about 350° to about 500° C.

9. A process according to claim 1, in which the alkyl alcohol is methanol and the co-reactant is a mixture of phenol and ortho-cresol.

10. A process according to claim 9, which comprises from about two to about six moles of methanol for each mole of phenol and ortho-cresol combined.

* * * * *